United States Patent [19]
Suciu-Foca et al.

[11] Patent Number: 4,818,689
[45] Date of Patent: Apr. 4, 1989

[54] LATE DIFFERENTIATION ANTIGEN ASSOCIATED WITH HELPER T LYMPHOCYTE FUNCTION

[75] Inventors: Nicole Suciu-Foca, Cliffside Park, N.J.; Donald W. King, Chicago, Ill.

[73] Assignee: The Trustees of Columbia University in the City of New York, New York, N.Y.

[21] Appl. No.: 752,397

[22] Filed: Jul. 5, 1985

[51] Int. Cl.$^4$ ............................................. G01N 33/53
[52] U.S. Cl. ........................................... 435/7; 435/4; 435/29; 435/34; 435/35; 436/519; 436/536; 436/542; 436/548
[58] Field of Search ...................... 435/4, 7, 29, 34, 35; 436/501, 519, 536, 542, 548

[56]  References Cited
U.S. PATENT DOCUMENTS

| 4,515,895 | 5/1985 | Kung et al. | 935/103 |
| 4,652,447 | 3/1987 | Kung et al. | 435/172.2 |
| 4,658,020 | 4/1987 | Kung et al. | 530/387 |
| 4,677,056 | 6/1987 | Dupont et al. | 435/29 |

OTHER PUBLICATIONS

Cotner, et al., J. Exp. Med., vol. 157, (1983), pp. 461-472.
Haars, et al., Immunogenetics, vol. 20, (1984), pp. 397-405.
Waldmann, et al., J. Clin. Invest., vol. 73, (1984), pp. 1711-1718.

Primary Examiner—Robert J. Warden
Assistant Examiner—Stephen C. Wieder
Attorney, Agent, or Firm—John P. White; John J. Santalone

[57] ABSTRACT

A late differentiation antigen ($LDA_1$) expressed by activated helper cells is described. $LDA_1$ is a membrane protein recognized by a monoclonal antibody produced by immunizing mice with an alloreactive human T cell clone with helper function. $LDA_1$ is expressed by helper T cells optionally 9 days after activation. Anti-$LDA_1$ monoclonal antibody blocks T cell enhancement of B-cell immunoglobulin production. Thus, $LDA_1$ is associated with helper T cell effector function. Methods of diagnosis and therapy based upon $LDA_1$ are also described.

2 Claims, 5 Drawing Sheets

EFFECT OF Mo Ab anti $LDA_1$ ON RATE OF GROWTH AND $^3$HTdR INCORPORATION OF AN ALLOREACTIVE TCL (NSF-K) PROPAGATED IN MEDIUM CONTAINING $IL_2$ AND ALLOGENEIC STIMULATING CELLS

LATE DIFFERENTIATION ANTIGEN ASSOCIATED WITH HELPER T LYMPHOCYTE FUNCTION

FIELD OF THE INVENTION

This invention is in the field of cellular immunology.

BACKGROUND OF THE INVENTION

There are three important subpopulations of T Lymphocytes (T cells): helper T cells, which interact with B cells to amplify production of antibody, effector T cells, which carry out the direct cell-killing function of T cells and make certain lymphokines (non-antibody products) which are responsible for delayed hypersensitivity, and suppressor T cells, which participate in the regulation of both antibody-medicated and cell-mediated immunity.

T cells must be activated before any of these forms of activity are expressed. Usually the activation follows from exposure to antigen, but other less specific factors such as interleukin 2 are also believed to participate in the activation of T cells Usually there is a latent period of around a week to 10 days after first exposure to antigen before the T cells develop initial reactivity. Shortly after that the reactivity subsides. But upon a second contact with antigen, T cells show an accelerated memory response with high activity developing within 2-5 days.

The addition of antigen to cultured lymphocytes induces a small proportion of T-cells to differentitate into the large rapidly dividing blast cells. T cells can also be transformed by culturing them together with the lymphocytes of individuals of the same species, a so-called mixed lymphocyte culture (MLC). Because of extensive polymorphism at HLA loci, the two cell populations are virtually always different antigenically and they stimulate each other to undergo blast transformation. For example, isolated blood lymphocytes from recipient and prospective donor are maintained together for several days in tissue culture. Blast transformation occurs if allogenic cells are present. This process may be referred to as alloactivation. One-way MLC's may be established is by treating one set of cells in a manner that prevents blast transformation of that set of cells such as irradiating the cells.

A T lymphocyte will recognize an antigen only if the antigen is properly presented by a presenting cell which in many cases is a macrophage. The antigen must be presented juxtaposed to a compatible Ia molecule, a surface molecule coded for by one of the class I transplantation or histocompatibility genes. In man, there are at least two distinct families of Ia molecules encoded by MHC genes, HLA-DR and MT or DS. These genes control the formation of the specialized complementary Ia structures on the surface of a presenting cell and the T cells hat provide for proper presentation of antigens. T cells may interact with B cells, or other T cells, of the cell possesses complementary Ia structures and if it recognizes the same antigenic determinant or a different determinant on the same antigenic molecule.

During the process of activation, T cells develop new surface antigens, so-called T cell activation antigens. Most of these T-cell activation antigens, however, are not T cell specific. For example, the transferrin receptor, the insulin receptor and the 4F2 antigen appear on proliferating cells of many types. Only one T cell activation antigen, Tac (Interleukin-2 receptor), is found only on activated T cells.

The kinetics of antigen appearance on activated T cells has been studied in order to gain some insight into the function of these molecules. Cotner et al., J. Exp. Med. 157: 461 (1983), examined the kinetics of appearance of several T cell antigens and found that each exhibited a characteristic and reproducible time of appearance. Based upon this, the antigens could be classified as early, intermediate or late appearing antigens.

The 4F2 antigen, Tac, the 49.9 antigen and the transferrin receptor appear within 24 hours of mitogen stimulation, before the onset of DNA synthesis, and are classified as early antigens. The authors postulate that the early appearing antigens may be associated with cell growth. The HLA-DR antigen and the 19.2 antigen (Ia antigen) do not appear until about 72 hours after activation and classified as late antigens. Expression of the OKT 10 antigen by activated T cells is intermediate.

The molecule or molecules associated with T cell helper function are unknown. Although human helper T cells are defined as lymphocytes which express the T4 surface antigen, this molecule is also found on killer and suppressor lymphoyctes suggesting that the T4 molecule is not involved in helper function. Similarly, the T cell antigen receptor does not seem to be involved in any specific T cell function because the gene which encodes the B-chain of the receptor is rearranged and expressed by helper, suppressor and cytotoxic T cells.

DISCLOSURE OF THE INVENTION

This invention pertains to a late appearing T cell differentiation antigen, designated $LDA_1$, which is expressed by activated human helper T-lymphocytes and is associated with the function of a T cells helper/inducer of B-lymphocyte immunoglobulin production. The invention also pertains to antibody against $LDA_1$ and to methods of therapy and diagnosis utilizing the antigen and antibody against it.

$LDA_1$ was identified as a membrane protein recognized by a murine monoclonal antibody produced in a mouse immunized with an alloreactive human helper T cell clone. $LDA_1$ is expressed mainly by T cells bearing the $T_4$ surface antigen i.e. by helper T cells. Studies of the kinetics of $LDA_1$ appearance show that $LDA_1$ is expressed by T cells optimally at about 9 days after in vitro activation with plant mitogens (e.g. PHA) and about 9 days after alloactivation in one-way mixed lymphocyte culture with allogeneic peripheral blood mononuclear cells. The antigen is not expressed by unactivated (resting) peripheral blood T or B lymphocytes or by Epstein-Barr virus (EBV) transformed B lymphoblastoid cell lines (LBCL).

$LDA_1$ is a surface protein comprised of two subunits of approximate molecular weight 100KD and 150KD. Utilizing anti-$LDA_1$, the antigen was immunoprecipitated by reacting the antibody with the immunizing helper T cell clone. The immunoprecipitated antigen was run on sodium dodecylsulfate polyacrylamide gel electrophoresesis. Two bands were identified as having the designated molecular weight.

Anti-$LDA_1$ monoclonal antibody blocks helper T cell enhancement of B-cell immunoglobulin production. In a Pokeweed mitogen, driven system, T cells induce immunoglobulin production by B-cells. Anti-$LDA_1$ antibody inhibits T cell inducement of Ig production in this system. IgG and particularly IgM production can be significantly reduced by the antibody.

The discovery of $LDA_1$ provides new procedures of diagnosis and therapy. $LDA_1$ is expressed by activated helper T cells and serves as a marker of these cell types. Assessment of $LDA_1$ expression can be an indicator of T cell hypoactivity or hyperactivity. The isolated antigen may have value therapeutic utility as a helper factor for amplifying immunoglobulin production. Anti-$LDA_1$ blocks the helper activity of T cells and can be used to supress the immune response. The antibody may be valuable in therapy of autoimmune disease and as an agent for inhibition of allograft rejection.

Figure 1A:
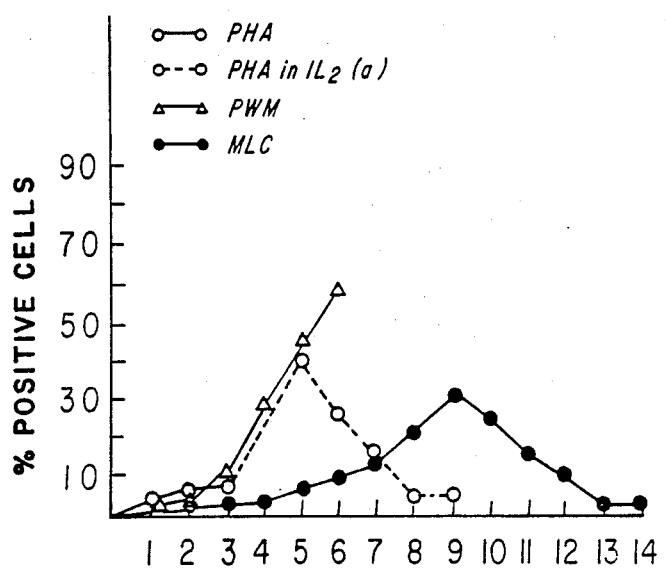
FIG. 1 illustrates the kinetics of expression of LDA1 on in vitro activated T lymphoblasts.

BEST MODE OF CARRYING OUT THE INVENTION $LDA_1$ is a T cell surface antigen which is characterized as follows:

a. $LDA_1$ is expressed by activated helper T cells, but not by resting peripheral T or B lymphocytes;

b, $LDA_1$ expression is expressed optimally by T cells nine days after stimulation in primary MLC culture;

c. $LDA_1$ expression is dependent upon DNA and protein synthesis by activated T cells;

d. Anti-$LDA_1$ antibody inhibits accelerated specific memory response to HLA-D/DR antigens when added to primary MLC cultures within the first 24 hours of primary stimulation; and e. Anti-$LDA_1$ antibody blocks helper T cell enhancement of immunoglobulin production of mitogen stimulated B cells.

The late expression of $LDA_1$ and the capability of anti-$LDA_1$ to block T cell helper function indicate that $LDA_1$ is a molecule associated with the effector function of helper T cells. The antigen may also be involved in specific memory responses.

As a molecule associated with helper T cell function, and perhaps directly responsible for it, the measurement of $LDA_1$ expression has diagnostic import. Because $LDA_1$ is distinctive to activated helper T cells, it is a unique marker for these cells and may be used to identify activated helper T cells in a population of lymphocytes. Moreover, the level of expression of $LDA_1$ provides a measure of helper T cell helper activity. This can be important information for evaluation of the immune an individual. For instance, in therapy of certain diseases, such as cancer, agents which affect the immuncompetency are often used. Assays $LDA_1$ expression may allow physicians to monitor the immune status of the patient and to adjust therapy to minimize the risk of opportunistic infection, often a threat to immunocomprimised patients.

The level of expression of $LDA_1$ can also be used in diagnosis of infection or of diseases related to T cell hypoactivity or hyperactivity. During bacterial or viral infection, helper T cell activity is generally increased as part of the immune response to the invading organisms. Increased $LDA_1$ expression associated with enhanced T cell activity can provide an indication of infection. In addition, certain autoimmune deseases are believed to be related to an hyperactive immune system. $LDA_1$ expression can provide an assessment of this hyperactivity.

Assays for $LDA_1$ expression can be conventional immunochemical assays for cell surface antigens. Anti-$LDA_1$ antibody is employed. Peripheral blood mononuclear cells can be isolated from a patient and incubated with anti-$LDA_1$ antibody under conditions which allow the antibody to bind the surface antigen. Antibody bound to the cell surface provides a measure of $LDA_1$ expression. Binding of the antibody to cells can be evaluated by employing an anti-$LDA_1$ antibody labeled with a radioactive, fluorescent or other compound which emits a delectable signal. Alternatively, a labeled second antibody against the anti-$LDA_1$ antibody may be used. For example, if the $LDA_1$ antibody is murine in origin, an anti-murine Ig antibody can be the second antibody. The second antibody is incubated with the cells after the anti-$LDA_1$ antibody and the cells are then evaluated for bound label.

$LDA_1$ may be a "helper factor" which mediates helper function. Thus, $LDA_1$ in soluble form may be a useful agent for modulating the immune response. For example, in immunodeficient persons, $LDA_1$ may be useful for restoring immunocompetency. In other situations where an enhanced immunity is desirable $LDA_1$ may be administered. For these purposes, $LDA_1$ can be administered in purified form in immunoenhancing amounts. Generally, $LDA_1$ would be given intravenously in a physiological acceptable vehicle.

Anti-$LDA_1$, which blocks the helper function of T cells, may also have therapeutic value. The antibody can be used to generally suppress immune response. In certain autoimmune deseases related to T cell hyperactivity, anti-$LDA_1$ may be effective in treatment. Additionally, the antibody may be useful in suppressing graft- versus-host reactions.

Antibody against $LDA_1$ can be produced in several ways. Polyclonal antibodies can be produced by immunizing animals with isolated $LDA_1$ by conventional techniques to produce polyclonal anti-$LDA_1$ antisera.

Monoclonal anti-$LDA_1$ antibodies are produced by antibody-producing cell lines. Anti-$LDA_1$ antibody-producing cell lines may be hybridoma cell lines commonly known as hybridomas. The hybrid cells are formed from the fusion of an anti-$LDA_1$ antibody-producing cell and an immortalizing cell line, that is, a cell line which imparts long term tissue culture stability on the hybrid cell. In the formation of the hybrid cell lines, the first fusion partner—the anti-$LDA_1$ antibody-producing cell may be a spleen cell of an animal immunized against $LDA_1$. Alternatively, the anti-$LDA_1$ antibody-producing cell may be an anti-$LDA_1$ generating B lymphocyte obtained from the spleen, peripheral blood, lymph nodes or other tissue. The second fusion partner—the immortal cell—may be a lymphoblastoid cell or a plasmacytoma cell such as a myeloma cell, itself an antibody-producing cell but also malignant.

Murine hybridomas which produce monoclonal anti-$LDA_1$ antibodies are formed by the fusion of mouse myeloma cells and spleen cells from mice immunized against $LDA_1$. To immunize the mice, a variety of different immunization protocols may be followed. For instance mice may receive primary and boosting immunizaitons $LDA_1$. The fusions are accomplished by standard procedure. Kohler and Milstein, (1975) Nature (London) 256, 495–497; Kennet, R., (1980) in Monoclonal Antibodies (Kennet et al., Eds. pp. 365–367, Plenum Press, N.Y.).

The hybridomas are then screened for production of antibody reactive with $LDA_1$. Those which secrete reactive antibodies are cloned.

Another way of forming the anti-$LDA_1$ antibody cell line is by transformation of antibody-producing cells. For example, an anti-$LDA_1$ antibody-producing B lymphocyte obtained from a human animal immunized against $LDA_1$, may be infected and transformed with a virus such as the Epstein-Barr virus in the case of human B lymphocytes to give an immortal anti-$LDA_1$ antibody-producing cell. See, e.g., Kozbor and Roder, (1983) *Immunology Today* 4(3), 72–79. Instead of infection with EBV, the B lymphocyte may be transformed by a transforming gene or tranforming gene product.

The monoclonal anti-$LDA_1$ antibodies can be produced in large quantities by injecting anti-$LDA_1$ 1 antibody-producing hybridomas into the peritoneal cavity of mice and, after an appropriate time, harvesting the ascites fluid which contains very high titer of homogenous antibody and isolating the monoclonal anti-$LDA_1$ antibodies therefrom. Xenogeneic hybridomas should be injected into irradiated or athymic nude mice. Alternatively, the antibodies may be produced by culturing anti-$LDA_1$ producing cells in vitro and isolating secreted monoclonal anti-$LDA_1$ antibodies from the cell culture medium.

Isolated $LDA_1$ can be produced by cloning and expressing the $LDA_1$ gene. The gene encoding $LDA_1$ can be identified and isolated by at least two techniques, the "cDNA" approach and the "genomic DNA" approach. For the "cDNA" approach, $LDA_1$ can be immunoprecipitated with anti-$LDA_1$. Immunoprecipitated $LDA_1$ can be isolated and partially sequenced. From the pro- tein sequence information, the possible nucleotide sequences of the $LDA_1$ gene can be predicted. DNA probes can be synthesized for all possibilities and used to screen a "cDNA" library of genes from activated T cells to identify clones carrying the $LDA_1$ gene or segments thereof. The library is constructed by synthesizing "cDNA" from mRNA of activated T cells bearing $LDA_1$ and inserting the "cDNA" into appropriate host cells. The gene can be isolated from the identified host and sequenced.

A second approach is the "genomic" approach. The DNA of T cells which express $LDA_1$ is isolated and fragmented. The fragmented DNA is used to transfect a non-human recipient cell line such as mouse fibroblast L cells which can express a foreign membrane protein on their membrane. The transfected clones are screened for expression of $LDA_1$ with anti-$LDA_1$ antibody. In the transfection procedure the recipient cell takes up a certain fraction of human DNA. In order to arrive at a clonal cell line which has essentially only the DNA of $LDA_1$ gene, the recipient cells expressing $LDA_1$ can be isolated and used to transfect a second recipient cell. The process can be repeated to segregate the $LDA_1$ gene in a cell. The gene can be then identified with human Alu sequence probes.

Once identified, the gene can be cloned and expressed in various host cell systems to provide ample quantities of $LDA_1$ as a soluble antigen for therapeutic and diagnostic uses. Conventional techniques and host/vectors systems can be employed.

The invention is illustrated further by the following Exemplification:

EXEMPLIFICATION

A. Production of anti-$LDA_1$ monoclonal antibody 1. Generation and Culture of human T-cell clones Peripheral blood mononuclear cells from individual M.W. (HLA-DR3,7) were primed in a 6-day mixed lymphocyte culture (MLC) against an equal number of irradiated lymphocytes from an HLA-DR half-identical allostimulator, individual R.C. (HLA-DR1,3). Lymphoblasts were isolated by differential centrifugation on a 55% isotonic percoll suspension (1.072 g/ml) followed by centrifugation through a 30% percoll suspension for removal of dead cell debris. The purified lymphoblasts were diluted to 33 cells/ml in RPMI 1640 medium supplmented with 20% T-cell growth factor (TCGF; Cellular Products, Buffalo, N.Y.), 15% heat-inactivated fetal calf serum (FCS), glutamine and antibiotics. Ten microliter aliquots were plated in sterile 60-well microtest II trays. To each well was added irradiated (4000 rad) B lymphoblasts (10,000 cells/well) obtained by Epstein-Barr virus (EBV) transformation of B cells from R.C. The wells that showed positive growth were transferred successively, at 7-day intervals, to 96- and 24- well trays and then to 25-$cm^2$ tissue culture flasks containing the appropriate concentration of TCGF and feeders. Selected clones were expanded by weekly restimulation with irradiated lymphoblastoid cells (LBCL) of stimulator origin. Clones were tested for MLC reactivity against the original stimulator in a 72-h blastogenesis assay, using as controls DW1/DR1-positive and DW1/DR1-negative stimulating cells (Eckels et al. 1983 Proc. Natl. Acad. Sci. U.S.A. 80: 830). Clone 19 was selected as an immunogen for preparation of T-cell receptor-specific antibodies, since it was exquisitely specific for DW1/DR1+-positive targets (r=0.86) C.

2. Immunization and Production of Monoclonal Antibodies

BALB/c mice were immunized three times. For each injection we used $7 \times 10^{66}$ cloned T cells (CTC) from the anti-DR1 clone 19 whose phenotype was OKT3+, OKT4+, OKT6−, OKT8−, OKT11+, Ia+. The last injection was given 2 days prior to fusion.

Splenocytes from immune BALB/c mice were fused with NS-1 plasmocytoma cells using the polythylene glycol fusion procedure (Kohler and Milstein, 1975 Nature 256: 495). Of 1900 wells seeded at $1 \times 10^4$ cells/well, 1700 wells showed hybridoma growth within 2 weeks. Culture supernatants were tested for antibody activity against human monocytes, T and B lymphocytes by complement-dependent lymphocytotoxicty using goat antimouse Ig immunoglobulin (GAMIG) for detection of noncytotoxic antibodies. Eight hundred and twenty hybridomas showing no reactivity with peripheral blood leukocytes were further tested by cytofluorometry on T lymphoblasts [MLC and phytohemagglutinin (PHA)-activated blasts], EBV-transformed B LBCL (including lines autologous to the T-cell clone and to its stimulator), T-cell leukemias, and T-cell clones.

Selected hybridomas which seemed to react with CTC 19 but not with other targets were cloned by limiting dilutions and injected into pristane-primed BALB/c mice. The resulting ascitic fluid was used as a source of antibody.

3. Cytofluorometric determination of the reactivity of Mo. Ab. 108.45 with T cells.

Monoclonal antibodies (Mo. Ab. 108.45) were tested for binding to cell-surface antigens by indirect immunofluorescence. One hundred thousand cells were incubated with 100ul hybridoma supernatant for 30 min at 4° C. in the presence of 10 ul human serum. The cells were washed three times with phosphate-buffered saline (PBS) containing 2.5% FCS and 0.05% $NaN_3$, and then incubated with 100 ul of a 1:40 dilution of FITC-conjugated GAMIG (Meloy, Springfield, Va.) for 30 min at 4° C. in the presence of human serum. Before analysis of binding on an Ortho Spectrum III Cytofluorometer, the cells were washed three times with PBS containing 2.5% FCS and 0.05% $NaN_3$ For direct immunofluoroescence, immunoglobulin was purified from the ascitic fluid of mice injected with the relevant hybridoma and conjugated with FITC by standard procedures.

Cytofluorometric determination of the reactivity of Mo. Ab. 108.45 with T cells. On intitial c=screening, 820 of the 1700 hybridomas failed to react with monocytes and T and B lymphocytes from an HLA reference panel of 50 individuals. As shown in Table 1, one of these 820 antibody-secreting hybridomas, No. 108, reacted with the immunizing B-lymphoblastoid lines or unrelated CTC. Following sequential subcloning, Mo. Ab. 108.45 was selected for further testing on 65 OKT4+ and 15 OKT8+ CTC derived from MLC blasts of M.W. (HLA-DR3,7) primed to R.C. (HLA-DR1,3). Mo. Ab. 108.45 reacted with 10 of 65 OKT4+ CTC (including CTC 19), but with no OKT8+ CTC. Six of these Mo. Ab. 108.45-positive CTC were twin clones of CTC 19. The remaining three derived from another MLC in which M.W. was primed to R.C. All of the Mo. Ab. 108.45-positive CTC were anti-DRI reactive, as determined by blastogenic responses to selected stimulators. There were, however, other CTC, which, although anti-DRI reactive, showed no binding of Mo. Ab. 108.45

Reactivity with $LDA_1$-MoAb was assessed daily by indirect immunofluorescense on a Spectrum III Cytofuuorometer using fluoroscein conjugated goat anti-mouse Ig (Cappel Lab., Cochranville) for staining the cells.

(a) PHA stimulated T lymphoblasts from 3-day cultures, were layered on a Percoll gradient, washed, resuspended at $10^6$ cells/ml and further propagated in culture medium containing 20% $IL_2$ (Biotest). (FIG. 1 upper panel)

T lymphoblasts ($10^6$ cell/ml) obtained from 6-day MLC by Percoll gradient centifugation were resuspended in "conditioned" medium containing 20% $IL_2$ and irradiated (2500r) PBM ($10^6$ cells/ml) from the original stimulating cell donor. Cultures were propagated by adding fresh conditioned medium every thrid day and irradiated stimulating cells every seventh day. $LDA_1$ expression was monitored weekly. Histograms show total number of T lymphoblasts (vertical axis) versus green fluorescence intensity (horizontal axis). Reactivity of MLC blasts with anti-$LDA_1$-MoAb following 2 and 3 weeks in culture is shown on the lower left and lower right panel respectively. (FIG. 1 lower panel)

Figure 1B:
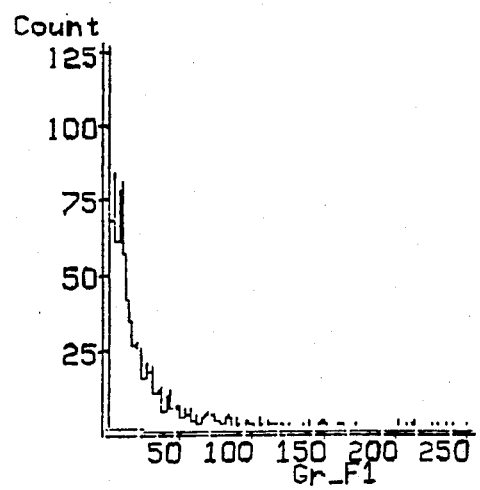
Figure 1B:
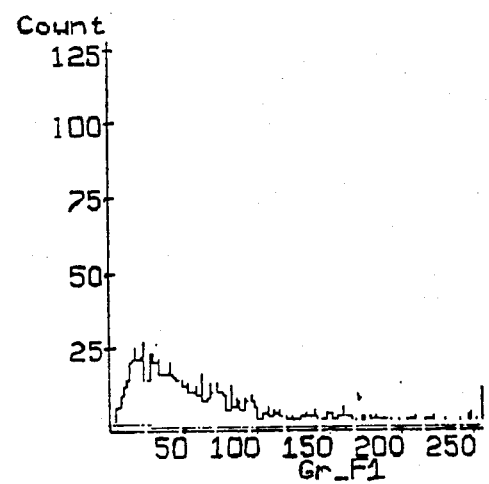

Results obtained with activated T cells from eight different individuals were very similar and are illustrated in FIG. 1. Less than 20% of the PHA activitated T lymphoblast express $LDA_1$ within the first 72 hours of incubation. When day-3-PHA-blasts were expanded in medium containing 20% $IL_2$ (Biotest), the fraction of the lymphoblast population on which $LDA_1$ was present increased to 40% by day-2, yet declined steadily thereafter, although the cells continued growing. To determine whether the expression of $LDA_1$ depends on cell proliferation and protein synthesis, day-3-PHA-blasts were incubated at 37° C. for 30 minutes with mitomycin C (25 $\mu g/ml$, Sigma Chemical Co., St. Louis, Mo.) or for two hours with emetine-HCL ($5\times10^6M$, Sigma Chemical Co.) then washed extensively, uultured in medium with IL2 and monitored by cytofluorometry for cell surface markers. $LDA_1$ induction seems dependent on protein synthesis since pretreatment with emetine, an irreversible inhibitor of pro-

TABLE 1

| | Cytofluorometric determination of reactivity of Mo 108 with human lymphocytes | | | | | | | |
|---|---|---|---|---|---|---|---|---|
| | Anti-$DR_1$ CTC from M.W. | | Unrelated alloreactive | MLC | PHA | T-cell | EBV transform | Normal PBL | |
| Targets | OKT4* | OKT8* | CTC | blasts | blasts | leukemias | B-cell lines | T cells | B cells |
| No. tested | 65 | 15 | 16 | 19 | 15 | 5 | 20 | 50 | 50 |
| No. reacting with Mo 108 | 10 | 0 | 0 | 0 | 0 | 0 | 0 | 0 | 0 |

B. Identification and Characterization of $LDA_1$

The expression of LDAhd 1 on T lymphocytes stimulated in vitro with plant mitogens or with irradiated allogeneic peripheral blood mononuclear cells (PHB) was monitored by indirect immunofluorescence on an Ortho Spectrum III Cytofluorometer as previously described Haars, R. et al. Immunogenetics 20: 397–405 (1984).

PBM ($10^6$ cell/ml) were incubated at 37° C. in a humidified 5% $CO_2$ atmosphere in RPMI 1640 medium supplemented with glutamine, antibiotics and 15% autologous plasma. Cultures were stimulated with PHA (1 ug/ml PHA/M Difco) PWM (10 ug/ml Pokeweed Mitogen, Grand Island Biological Co.) or irradiated HLA-D/DR different allogeneic cells ($10^6$ cells/ml).

tein synthesis at the level of translation or with mitomycin C, a potent inhibitor of DNA synthesis, prevented the proliferative response and expression of $LDA_1$ on cells which stayed viable for 72 hours. (Welte, K. et al. 1984, J. Exp. Med. 160: 1390) The anti-$LDA_1$ MoAb had no effect on the blastogenic response to PHA of T lymphocytes from fresh PBM.

Cytofluorometric evaluation of $LDA_1$ expression on cells grown in primary MLC culture showed that the percent $LDA_1$ positive T blasts reaches 30 by day-9 and decreases to background levels by day-14 (FIG. 1). The fraction of the population expressing $LDA_1$ was increased, however, to 70% when day-6 HLC-T lymphoblasts were expanded by continuous stimulation with irradiated cells from the sensitizing donor in IL2 supplemented medium (FIG. 1).

To determine whether the percent LDA$_1$ positive cells can be further increased, T cell lines TCL which have been grown for one month in medium containing IL$_2$ and stimulating cells and expressed LDA$_1$ on 70% of the cells, were subjected to sorting experiments by utilizing a fluorescence-activated cell sorter (FACS-I; Becton-Dickinson, Mountain View, Calif.). Sorted cells were cultured at 37° in medium containing IL$_2$ in the presence of an equal number of irradiated PBM from the stimulating cell donor. Both the positive T lymphoblasts after 48 hours, and 60±15% positive cells 120 hours following sorting. This indicates that LDA$_1$ modulates on the surface of the alloactivated T lymphoblasts by which it is synthesized.

When added at the initiation of primary MLC cultures, the anti-LDA$_1$-MoAb did not inhibit significantly the primary day-5-blastogenic response which was assessed by the rate of $^3$HTdR incorporation.

Since the expression of LDA$_1$ is acquired only during late stages of the primary MLC response (day-9), the effect of anti-MoAb on secondary MLC reactions was investigated. Lymphocytes from a responder with the HLA-DR5,9 phenotype were primed in MLC to HLA-DR5,7 stimulating cells. Monoclonal antibody anti-LDA$_1$ was added to individual cultures on day 0, 1, 2, 3, 4 or 5. The secondary MLC response was tested on day 10 by rechallenging the cultures with stimulating cells. Ten days after the initiation of the primary cultures, cells were collected from each flask, centrifuged on a Ficoll gradient for removal of dead cell debris, adjusted to 5×10$^4$ viable responding cells per microtest well and challenged in triplicate reactions with HLA-DR7 positive or DR7 negative stimulating cells. Secondary cultures were labeled with $^3$H-TdR for 18 hours and harvested on day-3 or on day-5 following restimulation. Results are expressed as mean CPM×10$^3$.

Figure 2:
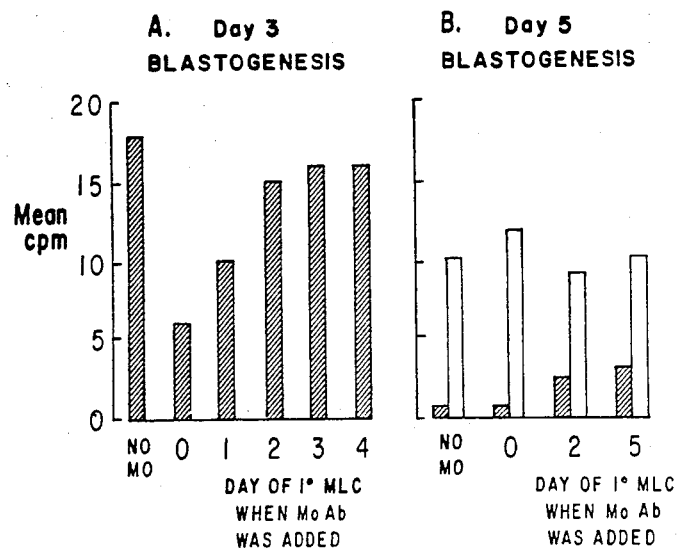
FIG. 2 shows the effect of anti-$LDA_1$ monoclonal antibody on secondary MLC responses.

The reaction to specific, HLA-DR7- positive stimulating cells was an accelerated memory response, which culminated on day-3 and declined by day-5. The day-3 response was strongly inhibited when the anti-LDA$_1$-MoAb was added to the cultures within the first 24 hours of primary stimulation but not when added later (FIG. 2A). None of the cultures showed accelerated (day-3) memory re- sponses to HLA-DR7 negative stimulating cells. They displayed, however, primary-type blastogenic re- sponses to such cells on day-5, as expected for polyclonal population of T cells which are capable to recognize any allelic variants of (non-self) HLA-D/DR antigens in primary cultures. This primary anti-DR blastogenic response was not significantly inhibited in cultures grown with anti-LDA$_1$-MoAb (FIG. 2B). It therefore appears that the anti-LDA$_1$- MoAb inhibits specific memory responses to HLA-D/DR antigens.

Figure 3:
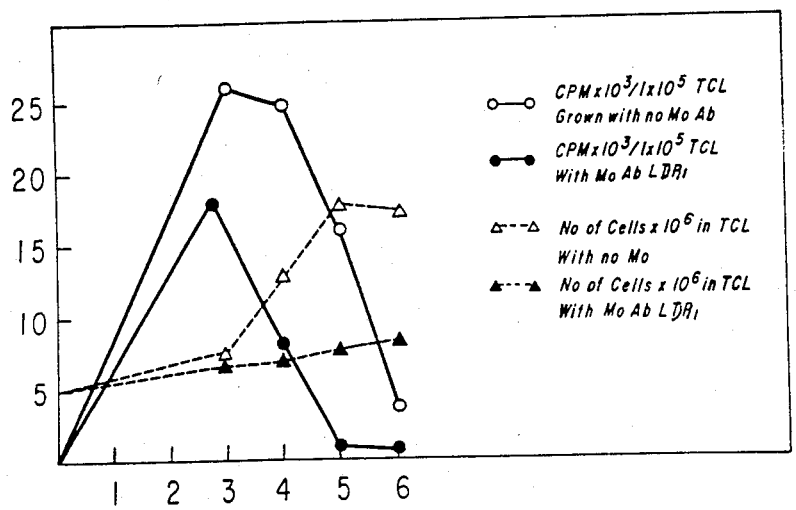
FIG. 3 illustrates the efftect of Mo Ab anti-$LDA_1$ on rate of growth and $^3HTdR$ incorporation of an alloreative TCL (NSF-K) propagated in medium containing $IL_2$ and allogeneic stimulating cells.

This possibility was further explored by determining the effect of the MoAb on three different anti-HLA-D/DR reactive "bulk" T cell lines and on two T cell clones derived from each of the lines. The NSF-K TCL was developed by priming PBL from an DR2 homozygous individual to irradiated PBL from a DR3 monozygous stimulator. Day-6 MLC blasts were progated for 28 days by weekly stimulation with DR3 positive cells in medium containing 20% IL$_2$. Responding T lymphoblasts (5×10$^6$ culture) were tested for reactivity to DR3 positive stimulating cells in the absence or in the presence of anti-LDA$_1$ MoAb (1:100 final dilution). The number of viable cells and the rate of $^3$H-TdR incorporation was determined on day 3–6. The antibody did not affect the IL$_2$ reactivity of such lines but inhibited strongly the blastogenic response to irradiated PBM from the stimulating cell donor, as quantitated by the rate of $^3$H-TdR incorporation (FIG. 3).

Since recognition of HLA-D/DR antigens by T lymphocytes is a prerequisite for activating their helper function and since specific anti-Ia responses are inhibited by anti-LDA$_1$ MoAb, experiments were performed to determine whether this monoclonal antibody also blocks the helper function of resting and allostimulated T lymphocytes.

The helper function of T lymphocytes can be easily quantitated by determining the capacity of T lymphocytes to induce B cell differentiation in a Pokeweed Mitogen (PWM) driven system. See Waldmann, T. A. et al. *J. Clin. Invest.* 73: 1711 (1984).

Although LDA$_1$ is expressed on a relatively high proportion of PWM stimulated T lymphoblasts (Fig.1), the anti-LDA$_1$-MoAb has no consistent inhibitory effect on blastogenic responses induced by PWM. This antibody blocks, however, the capacity of helper T cells to enhance immunoglobulin production by autologous PWM stimulated B-cells (Table 1). Thus, the amount of IgG and particularly of IgM in supernatants of cultures containig PBM stimulated for 6 days with PWM in the presence of anti-LDAs MoAbs was significantly lower than the amount found in control cultures containing no MoAbs or two other newly developed MoAbs which recognize late T-cell differentiation antigens.

TABLE 2

| Individual no | IgM (ng/ml) in cultures tested | | IgG (ng/ml) in cultures tested | |
|---|---|---|---|---|
| | WITHOUT Anti-LDA$_1$ | WITH MoAb | WITHOUT Anti-LDA$_1$ | WITH MoAb |
| 1 | 8 | 0 | 50 | 2.5 |
| 2 | 2 | 0 | 50 | 1.5 |
| 3 | 35 | 2 | 60 | 3 |
| 4 | 25 | 0 | 20 | 1 |
| 5 | 35 | 0 | 60 | 3 |
| 6 | 9 | 0 | 200 | 7.5 |

PBM (1 × 10$^5$/reaction form 6 different responders were cultured in round bottom microculture plate at 37° C. in a humidified 5% CO$_2$ atmosphere in RPMI 1640 medium supplemented with 15% heat inactivated fetal calf serum (FCS), 200 mM L-glutamine, 25 mHEPES buffer and 1% penicillin/streptomycin. PWM was added to the cultures at a final concentration of 10 ug/ml. Replicate cultures were grown with or without anti-LDA$_1$-MoAb. The amount of IgG and IgM contained in 50 lambda aliquots of day-6 culture supernatent was quantitated in round-bottom polyvinyl trays (Costar) coated with rabbit anti-human IgG or IgM (Dako Accurate Chemicals. Known amounts of human IgG or IgM in the same medium were tested as standards. Triplicate wells were used for each reaction. Following two hours of incubation, wells were emptied, washed in 1% FCS in PBS and covered with 50 lambda of a 1:3000 or 1:1000 dilution of Peroxidase Conjugated rabbit anti-human IgG or IgM respectively. Trays were incubated for one hour at room temperature in the dark, then washed five times in 1% FCS/PBS. Fifty microliters of ABTS (2,2 azino-di) (3 ethylbenzthia zoline sulphonic acid) diluted 1:100 in 0.1 M citrate buffer (pH 4.2) containing 0.03% Hydrogen Peroxidase were added to each well. Following 30 minutes of incubation at room temperature in the dark, 50 lambda of a 1% solution of sodium dodecyl sulphate were added to stop the reaction. The absorbance at 405 nanometers was read with an automated photometer (Flow Multiskan).

Figure 4:
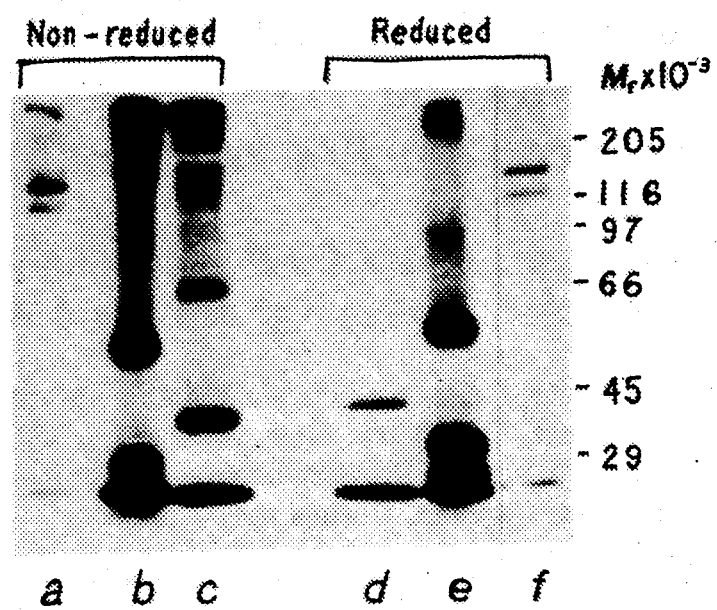
FIG. 4 is a SDS-PAGE gel autoradiograph of $^{125}I$ labeled membrane proteins of TCC #19 cells.

Similar results were obtained when alloreactive T cell clones with high anti-HLAD/DR reactivity and helper function were cultured with stimulator-type B cells, in medium containing PWM. Supernatants from cultures to which anti-LDA$_1$ MoAbs was added, contained 80±10% less human immunoglobulin than supernatants from replicate, control cultures without MoAb. Immunoprecipitation studies of the molecule recognized by the anti-LDA$_1$-MoAb were performed using $^{125}$I-labeled extracts from the immunizing TCL (16). 20×10$^6$ cells were surface labelled with 1 mCi of Na$^{125}$I (Amersham) using the lactoperoxidase technique as previously described. Haars et al. Supra. The labelled cells were washed and lysed in 0.5 ml. of 100 mM Tris HCL, pH 7.4/1 mM phenylmethylsulfonyl fluoride/ 1mM EDTA/ 0.5% Triton X-100. Cell lysate was centrifuged at 40,000×g for 30 minutes and the supernatent was filtered through a 0.2 μm millipore filter. The filtered supernatant was precleared 3 times by sequential 1 hour incubation at 4° C. with protein A-sepharose, rabbit anti-mouse IgG coupled sepharose and an irrelevant monoclonal antibody coupled to sepharose. The precleared cell lysate supernatant was incubated for 4 hours with specific antibody coupled to sepharose 4B, following the immunoprecipitation procedure described before. Harris et al. Supra. Immune precipitated were then processed for SDS-PAGE in the presence (reducing condition) of 5% 2-mercaptoethanol using 7.5% polyacrylamide gel. (A,F) MoAb anti-LDA$_1$ (B,E) MoAb A3 to a framework determinant of human MHC Class II antigen and (C,D) MoAv NAM 1 to human B$_2$ microglobulin. Two bands of MW 110 and 150 KD approximately were found under reducing and nonreducing conditions (FIG. 4).

Taken together these data indicate that LDA$_1$ is a late differentiation cell surface protein expressed by T lymphoblasts with anti-HLA-D/DR reactivity and helper inducer function. This antigen may be encoded by a "helper" function gene or by a T-cell receptor gene (possible Fc) involved in antibody production and isotype class switching.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of diagnosing the immune system of a patient by assessing the level of helper T cell activity which comprises:
    (a) obtaining from the patient a sample of peripheral blood mononuclear cells containing T lymphocytes;
    (b) contacting the sample under appropriate conditions with a monoclonal antibody that specifically binds to LDA$_1$ (a late appearing T lymphoctyes), so as to form a detectable complex between the monoclonal antibody and the expressed LDA$_1$;
    (c) quantitatively detecting the complex, thereby quantitatively determining the amount of LDA$_1$ present and the activity of the helper T lymphocytes present in the sample; and
    (d) comparing the activity of the helper T lymphocytes present in the sample with a reference thereby diagnosing the immune system of the patient.

2. A method of claim 1, wherein the monoclonal antibody is radiatively or fluorescently labelled.

* * * * *